United States Patent [19]
Mausner

[11] Patent Number: 5,352,441
[45] Date of Patent: Oct. 4, 1994

[54] POWDER-BASED LIP LINER COSMETIC COMPOSITION

[75] Inventor: Jack Mausner, New York, N.Y.

[73] Assignee: Chanel, Inc., Piscataway, N.J.

[21] Appl. No.: 119,037

[22] Filed: Sep. 9, 1993

[51] Int. Cl.$^5$ .............................................. A61K 7/025
[52] U.S. Cl. ........................................ 424/64; 424/63; 424/490; 424/682; 514/772.3; 514/772.5
[58] Field of Search ................... 424/63, 64, 682, 490; 514/772.3, 772.5

[56] References Cited

U.S. PATENT DOCUMENTS

| | | | |
|---|---|---|---|
| 3,697,643 | 10/1972 | Shepherd et al. | 424/63 |
| 3,864,275 | 2/1975 | Kan et al. | 252/316 |
| 3,911,105 | 10/1975 | Papantoniou et al. | 424/64 |
| 3,966,398 | 6/1976 | Vanlerberghe et al. | 8/11 |
| 4,125,549 | 11/1978 | Coopersmith et al. | 260/425 |
| 4,247,411 | 1/1981 | Vanlerberghe et al. | 252/316 |
| 4,369,037 | 1/1983 | Matsunaga et al. | 8/127.51 |
| 4,400,295 | 8/1983 | Ootsu et al. | 252/356 |
| 4,423,031 | 12/1983 | Murui et al. | 424/63 |
| 4,460,371 | 7/1984 | Abber | 604/897 |
| 4,481,186 | 11/1984 | Deckner | 424/59 |
| 4,549,990 | 10/1985 | Seguin et al. | 260/397.25 |
| 4,574,082 | 3/1986 | Tietjen et al. | 424/63 |
| 4,608,392 | 8/1986 | Jacquet et al. | 514/844 |
| 4,752,496 | 6/1988 | Fellows et al. | 427/27 |
| 4,758,599 | 7/1988 | Minetti | 514/844 |
| 4,820,510 | 4/1989 | Arraudeau et al. | 424/63 |
| 4,883,659 | 11/1989 | Goodman et al. | 424/78 |
| 4,925,667 | 5/1990 | Fellows et al. | 424/401 |
| 4,927,952 | 5/1990 | Gueyne et al. | 556/419 |
| 4,952,560 | 8/1990 | Kigasawa et al. | 514/2 |
| 4,980,155 | 12/1990 | Shah et al. | 424/63 |
| 4,988,502 | 1/1991 | Ounanian et al. | 424/63 |
| 5,034,226 | 7/1991 | Beck | 424/195.1 |
| 5,037,803 | 8/1991 | Gueyne et al. | 514/2 |
| 5,053,220 | 10/1991 | Arraudeau et al. | 424/63 |
| 5,053,221 | 10/1991 | Robertson et al. | 424/63 |
| 5,061,481 | 10/1991 | Suzuki et al. | 424/63 |

*Primary Examiner*—Thurman K. Page
*Assistant Examiner*—Jyothsna Venkat
*Attorney, Agent, or Firm*—Merchant, Gould, Smith, Edell, Welter & Schmidt

[57] ABSTRACT

A powder-based lip liner cosmetic composition comprises: (1) a talc component; (2) a mica component; (3) a low luster pigment; (4) a substantially hydrophobic polymer; (5) an at least partially hydrophilic polymer; and (6) an emulsifier component. Preferably, the talc component includes talc coated with an aluminum salt of a long-chain fatty acid. Preferably, the mica component includes mica coated with an aluminum salt of a long-chain fatty acid. Preferably, the low luster pigment includes mica, titanium dioxide, and barium sulfate. Preferably, the cosmetic composition further comprises a skin-tone-dependent pigment, as well as ancillary components. The lip liner cosmetic composition of the present invention provides a long lasting lip line resistant to contact with surfaces and eliminates the problem of "bleeding" or "feathering" of lipstick into the lip liner. This is achieved by the insolubility of lipstick in the lip liner because of the low wax and oil content of the lip liner of the present invention. The lip liner of the present invention is preferably applied by the use of a water-wetted brush, unlike any other lip liners previously available.

31 Claims, No Drawings

POWDER-BASED LIP LINER COSMETIC COMPOSITION

BACKGROUND

This invention is directed to a powder-based lip liner cosmetic composition.

The great majority of existing lip liners are in pencil form. The composition of these pencils consists of necessarily large proportions of oils, waxes, and fats, plus other emollient materials which deposit a waxy or oily, non-dry film. The latter film is removable on contact with any surface, such as glass or plastic. The film is moreover permeable to lipstick and color and therefore is not totally satisfactory in preventing "bleeding" or "feathering" of the color above or below the lip line. This is because of the high solubility of lipstick into the wax and oil-based conventional lip liner.

A minor proportion of lip liners are thick liquids similar in composition to that of pencils, which are applied with a brush. The characteristics and properties of these liquid lip liners are almost identical to those of the lip liner pencils. However, the oil content is even higher in liquid lip liners than in pencils, which aggravates even further the problems of "feathering" and excessively rapid removal.

There is therefore a need for an improved lip liner that is long lasting and not easily removable in contact with surfaces. In particular, there is a need for an improved lip liner that is impermeable to lipstick and prevents the typical "feathering" or "bleeding" of lipstick compositions when applied next to lip liner. Additionally, there is a need for an improved lip liner composition that is substantially dry and powdery in form which contains low levels of oil and waxes. There is furthermore a need for a lip liner that can be readily applied creating a smooth and desirable appearance.

SUMMARY

I have developed a powder-based lip liner cosmetic composition incorporating a new combination of ingredients. The lip liner cosmetic composition of the present invention provides a long lasting lip line resistant to contact with surfaces and eliminates the problem of "bleeding" or "feathering" of lipstick into lip liner and above and below the lip line. This is achieved by the insolubility of lipstick in the lip liner because of the low wax and oil content of the lip liner of the present invention.

The composition of the lip liner of the present invention is such that it is preferably applied to the lips with the aid of a water-wetted brush. This method of application is unlike that of previously-existing lip liners.

In general, the powder-based lip liner cosmetic composition of the present invention comprises:
(1) a talc component;
(2) a mica component;
(3) a low luster pigment;
(4) a substantially hydrophobic polymer;
(5) an at least partially hydrophilic polymer; and
(6) an emulsifier component.

The talc component, the mica component, the low-luster pigment, the substantially hydrophobic polymer, and the at least partially hydrophilic polymer are each present in a quantity sufficient to contribute to the appearance of the lips of a wearer to whom the composition is applied. The emulsifier is present in a quantity sufficient to emulsify the components including the substantially hydrophobic polymer and the at least partially hydrophilic polymer.

Preferably, the talc component includes talc coated with an aluminum salt of a long-chain fatty acid. Preferably, the mica component includes mica coated with an aluminum salt of a long-chain fatty acid.

Preferably, the aluminum salt of the long-chain fatty acid coating the talc and the mica is selected from the group consisting of aluminum myristate, aluminum laurate, and aluminum palmitate. Most preferably, it is aluminum myristate.

Preferably, the substantially hydrophobic polymer is a copolymer of polyvinylpyrrolidone and hexadecene.

Preferably, the at least partially hydrophilic polymer comprises butylated polyvinylpyrrolidone.

Preferably, the composition comprises at least one skin tone-dependent pigment in order to customize the composition for the skin tone and/or complexion of the wearer. The skin-tone-dependent pigment preferably is selected from the group consisting of D & C Red No. 6, brown iron oxide and red iron oxide.

Preferably, the emulsifier component comprises at least one of sorbitan laurate, polysorbate 20, glyceryl monooleate, and tocopheryl acetate. Most preferably, the emulsifier component comprises all of sorbitan laurate, polysorbate 20, glyceryl monooleate, and tocopheryl acetate.

The cosmetic composition of the present invention also preferably includes ancillary components. These components include: (1) lauroyl lysine; (2) a magnesium salt of a long-chain fatty acid selected from the group consisting of magnesium stearate, magnesium palmitate, and magnesium arachidate; (3) a preservative component; (4) trisodium ethylenediaminetetraacetate; and (5) diisopropyl dimerate. Preferably, the magnesium salt of the long-chain fatty acid is magnesium stearate. Preferably, the composition includes all of these ancillary components.

A preferred lip liner composition according to the present invention comprises:
(1) about 10% to about 25% of a talc component including talc coated with aluminum myristate;
(2) about 5% to about 15% of lauroyl lysine;
(3) about 10% to about 30% of a mica component comprising mica coated with aluminum myristate;
(4) about 2% to about 10% of magnesium stearate;
(5) about 5% to about 15% of a low-luster pigment comprising mica, titanium dioxide, and barium sulfate;
(6) about 0.1% to about 1% of sodium dehydroacetate;
(7) about 0.05% to about 0.5% of trisodium ethylenediaminetetraacetate;
(8) about 1% to about 5% of an at least partially hydrophilic polymer including butylated polyvinylpyrrolidone;
(9) up to about 15% of D & C red No. 6;
(10) up to about 15% of brown iron oxide;
(11) up to about 15% of red iron oxide;
(12) from about 1% to about 5% of sorbitan laurate;
(13) from about 1% to about 5% of polysorbate 20;
(14) from about 1% to about 5% of glyceryl monooleate;
(15) from about 0.5% to about 1% of tocopheryl acetate;
(16) from about 3% to about 8% of diisopropyl dimerate; and

(17) from about 1% to about 5% of a substantially hydrophobic polymer including a copolymer of polyvinylpyrrolidone and hexadecene.

DESCRIPTION

A new combination of ingredients results in a powder-based lip liner in a pressed cake form. The lip liner is uniquely applied via a water-wet brush, with an emulsion being formed in situ on the cake. The lip liner is then applied as a thin line to the outline of the lips. The product is primarily formulated of dry powders with a very low level of oils and with a total absence of typical waxes. The resulting product, when applied, is very long lasting, not easily removable in contact with surfaces, and substantially impermeable to lipstick because of the insolubility of lipstick in the product. This eliminates the usual migration of lipstick above and below the lip line.

The lip liner composition of the present invention comprises:

(1) a talc component;
(2) a mica component;
(3) a low luster pigment;
(4) at least one substantially hydrophobic polymer;
(5) at least one partially hydrophilic polymer; and
(6) an emulsifier component.

The talc component, the mica component, the low luster pigment, the substantially hydrophobic polymer, and the at least partially hydrophilic polymer are each present in a quantity sufficient to contribute to the appearance of the lips of the wearer to whom the composition is applied. The emulsifier is present in a quantity sufficient to emulsify the substantially hydrophobic polymer and the at least partially hydrophilic polymer.

Preferably, the talc component includes talc coated with an aluminum salt of a long-chain fatty acid. Preferably, the mica component includes mica coated with an aluminum salt of a long-chain fatty acid. The particle size of the talc component and the mica component is preferably from about 1 to about 20 microns. Typically, mica comprises about 22% of the mica component. The proportion of talc in the talc component varies according to the shade of the cosmetic composition. A supplier of suitable mica and talc components is U.S. Cosmetics (Putnam, Conn.).

The aluminum salt of a long-chain fatty acid preferably included in the talc and mica components is preferably aluminum laurate, aluminum myristate, or aluminum palmitate. Preferably, the aluminum salt is aluminum myristate for both the talc component and the mica component.

The substantially hydrophobic polymer is preferably a copolymer of polyvinylpyrrolidone and hexadecene. Most preferably, the polyvinylpyrrolidone/hexadecene copolymer has a proportion of polyvinylpyrrolidone to hexadecene of about 1:4 on a moles of monomer basis. Preferably, the molecular weight of the copolymer is about 7,300. A suitable copolymer is known as Ganex V-216, distributed by GAF Corporation, Wayne, N.J. Less preferably, other long-chain monoalkenes, such as pentadecene or heptadecene, can be substituted for hexadecene in the copolymer.

The low luster pigment is preferably mica, titanium oxide, and barium sulfate. Preferably, the proportion of these ingredients are about 46% to about 60% mica, about 15% to about 22% titanium dioxide, and about 25% to about 32% barium sulfate on a weight basis. Less preferably, other alkaline earth sulfates, such as calcium sulfate, can substitute for barium sulfate in the low luster pigment.

The at least partially hydrophilic polymer is preferably butylated polyvinylpyrrolidone. Less preferably, other substituted polyvinylpyrrolidones, such as propylated polyvinylpyrrolidone, can substitute for butylated polyvinylpyrrolidone as the at least partially hydrophilic polymer. Preferably, the butylated polyvinylpyrrolidone has a molecular weight of about 16,000. A suitable copolymer is known as Ganex P-904, distributed by GAF Corporation, Wayne, N.J.

Preferably, the composition of the present invention comprises from about 10% to about 25% of talc coated with aluminum myristate, about 10% to about 30% of mica coated with aluminum myristate, about 5% to about 15% of a low luster pigment including mica, titanium dioxide and barium sulfate, about 1% to about 5% of butylated polyvinylpyrrolidone, and about 1% to about 5% of a polyvinylpyrrolidone/hexadecene copolymer.

The emulsifier component is preferably at least one of sorbitan laurate, polysorbate 20, glyceryl monooleate, and tocopheryl acetate. Preferably, the composition includes all of sorbitan laurate, polysorbate 20, glyceryl monooleate, and tocopheryl acetate. Most preferably, the composition includes from about 1% to about 5% of sorbitan laurate, from about 1% to about 5% of polysorbate 20, from about 1% to about 5% of glyceryl monooleate, and from about 0.5% to about 1% of tocopheryl acetate. Less preferably, glyceryl esters of other long-chain unsaturated or saturated fatty acids can replace the glyceryl monooleate. Such glyceryl esters include glyceryl stearate, glyceryl linoleate, or glyceryl linolenate.

Preferably, the cosmetic composition of the present invention further comprises an additional cosmetic component, a skin-tone-dependent pigment. Preferably, this pigment comprises at least one of D & C Red #6, brown iron oxide, and red iron oxide. The relative proportions of each of these ingredients can be adjusted for the skin tone and/or complexion of the user, so that the composition can be customized to some extent to suit individual users. A large number of formulations are therefore possible and are included within the scope of the present invention. Preferably, the cosmetic composition of the present invention contains up to about 15% of each of D & C Red #6, brown iron oxide, and red iron oxide. A suitable brown iron oxide and red iron oxide for use in a cosmetic composition according to the present invention are available under the trade name of Amihope, supplied by Ajinomoto Co., Tokyo, Japan. The brown iron oxide and red iron oxide are treated for use in cosmetic compositions.

Besides the cosmetic components and the emulsifier, the lip liner composition of the present invention preferably includes ancillary components. The use of these ancillary components is optional but preferable. These components can include:

(1) lauroyl lysine;
(2) magnesium stearate;
(3) a preservative component;
(4) trisodium ethylenediaminetetraacetate; and
(5) diisopropyl dimerate.

Preferably, the cosmetic composition includes all of these ancillary components.

Preferably, the cosmetic composition includes lauroyl lysine. Most preferably, the composition includes from about 5% to about 15% of lauroyl lysine.

Preferably, the composition includes magnesium stearate. Most preferably, the composition includes from about 2% to about 10% of magnesium stearate. Less preferably, a magnesium salt of another long-chain fatty acid can be substituted for the magnesium stearate, such as magnesium palmitate or magnesium arachidate.

The composition preferably includes a preservative component. Preferably, the preservative is sodium dehydroacetate. Most preferably, the composition includes from about 0.1% to about 1.0% of sodium dehydroacetate. Other preservative components known in the art can also be used in place of or in addition to sodium dehydroacetate.

Preferably, the composition also includes trisodium ethylenediaminetetraacetate. Most preferably, the composition includes from about 0.05% to about 0.5% of trisodium ethylenediaminetetraacetate.

Preferably, the composition includes diisopropyl dimerate. Most preferably, the composition includes from about 3% to about 8% of diisopropyl dimerate.

The preferred concentrations of both the cosmetic components and the ancillary components are shown in Table I. Also shown in table I are the mixtures of which each component is a part for the preparation of the composition as discussed below.

TABLE I

COMPONENTS OF A PREFERRED LIP LINER COSMETIC COMPOSITION ACCORDING TO THE PRESENT INVENTION

| MIXTURE | COMPONENT | PERCENTAGE RANGE |
|---|---|---|
| I | Aluminum myristate coated talc | 10–25 |
| I | Lauroyl lysine | 5–15 |
| I | Aluminum myristate coated mica | 10–30 |
| I | Magnesium stearate | 2–10 |
| I | Low luster pigment including mica, titanium dioxide, and barium sulfate | 5–15 |
| I | Sodium dehydroacetate | 0.1–1.0 |
| I | Trisodium ethylenediaminetetraacetate | 0.05–0.50 |
| I | Butylated polyvinylpyrrolidone | 1–5 |
| I | D & C Red #6 | 0–15 |
| I | Brown iron oxide | 0–15 |
| I | Red iron oxide | 0–15 |
| II | Sorbitan laurate | 1–5 |
| II | Polysorbate 20 | 1–5 |
| II | Glyceryl monooleate | 1–5 |
| II | Tocopheryl acetate | 0.5–1.0 |
| II | Diisopropyl dimerate | 3–8 |
| II | Polyvinylpyrrolidone/ hexadecene copolymer | 1–5 |

The various mixtures and the sequence in which they are prepared and combined for the preparation of the lip liner of the present invention are now described in some detail. The object of the mixing sequence is to prepare a smooth and homogeneous composition that is thoroughly pulverized.

Mixture I is placed in a PK mixer, which is a twin shell blender manufactured by Patterson-Kelley (East Stroudsburg, Pa.). The mixture is then mixed for 5 minutes with the mixing bar on, then tumbled 15 minutes without the bar. Mixture I is then micropulverized twice through a 0.027 inch screen, and the degree of pulverization is checked. When the degree of pulverization is satisfactory, the mixture is placed back into the PK mixer. Mixture II is placed into a suitable mixing vessel, heated to 45°–50° C. and mixed for 10 minutes. Approximately two-thirds of Mixture II is then added to Mixture I through the mixing bar of the PK mixer. The combination is then mixed with the bar on for 3 minutes. An additional one-sixth of Mixture II is then added to Mixture I through the mixing bar of the PK mixer, and the combination is then mixed with the bar on for 3 minutes. Finally, the remaining one-sixth of Mixture II is added to Mixture I, with repeated mixing through the mixing bar for 3 minutes. The entire batch is then mixed for an additional 5 minutes with the mixing bar. An aliquot of about 1 kilogram is then micropulverized once through a 0.027 inch screen and the color of the batch is checked. When the color is suitable, the remainder of the batch is then pulverized. The resulting lip liner composition is stable.

In use, the lip liner is supplied to the consumer as a pressed cake. It is uniquely applied to the lips via a water-wet brush, with an emulsion being formed in situ on the cake. The product is then applied as a thin line to the outline of the lips. The emulsifiers are present to enable the emulsion to be created in situ with the water being applied by the wet brush.

ADVANTAGES OF THE INVENTION

The lip liner cosmetic composition of the present invention effectively accentuates the margin of the lips to provide a clear border line for lipstick and uniquely prevents the "bleeding" or "feathering" of lipstick and color into the crevices above and below the lip line. Because of the very low level of oils and the total absence of typical waxes in the preparation, together with the presence of dry powders, the line created by the use of the lip liner cosmetic composition of the present invention on the lips is dry and powdery and is therefore impermeable to lipstick, unlike conventional lip liners, very long lasting and not easily removable in contact with surfaces.

This composition, therefore, prevents "feathering" and "bleeding" of lipstick compositions in to or through the lip liner. This invention provides important advantages to lipstick wearers who object to the migration of lipstick and color into the upper and lower crevices of lips and the short longevity of the lip line with conventional lip liners.

Although the present invention has been described in considerable detail with regard to certain preferred version thereof, other versions are possible. Therefore, the spirit and scope of the appended claims should not be limited to the description of the preferred version contained herein.

I claim:

1. A powder-based lip liner cosmetic composition comprising:
   (a) talc coated with an aluminum salt of a long-chain fatty acid;
   (b) mica coated with an aluminum salt of a long-chain fatty acid;
   (c) low luster pigment which includes mica, titanium dioxide and barium sulfate;
   (d) a substantially hydrophobic polymer selected from the group consisting of a copolymer of polyvinylpyrrolidone and hexadecene, a copolymer of polyvinylpyrrolidone and pentadecene, and a copolymer of polyvinylpyrrolidone and heptadecene;
   (e) hydrophilic polymer selected from the group consisting of butylated polyvinylpyrrolidone and propylated polyvinylpyrrolidone; and
   (f) an emulsifier component; the talc component, the mica component, the low-luster pigment, the substantially hydrophobic polymer, and the hydrophilic polymer each being present in a quantity sufficient to contribute to the appearance of the lips of a wearer to whom the composition is applied, and the emulsifier being present in a quantity sufficient to emulsify the components including the substantially hydrophobic polymer and the hydrophilic polymer.

2. The cosmetic composition of claim 1 wherein the aluminum salt of the long-chain fatty acid coating the talc is selected from the group consisting of aluminum myristate, aluminum laurate and aluminum palmitate.

3. The cosmetic composition of claim 2 wherein the aluminum salt of the long-chain fatty acid coating the talc is aluminum myristate.

4. The cosmetic composition of claim 1 wherein the aluminum salt of the long-chain fatty acid coating the mica is selected from the group consisting of aluminum laurate, aluminum myristate and aluminum palmitate.

5. The cosmetic composition of claim 4 wherein the aluminum salt of the long-chain fatty acid coating the mica is aluminum myristate.

6. The cosmetic composition of claim 1 wherein the substantially hydrophobic polymer is a copolymer of polyvinylpyrrolidone and hexadecene.

7. The cosmetic composition of claim 1 wherein the hydrophilic polymer is butylated polyvinylpyrrolidone.

8. The cosmetic composition of claim 1 further comprising skin tone-dependent pigment.

9. The cosmetic composition of claim 8 wherein the skin-tone-dependent pigment is selected from the group consisting of D & C Red No. 6, brown iron oxide and red iron oxide.

10. The cosmetic composition of claim 1 comprising talc coated by aluminum myristate, mica coated by aluminum myristate, the substantially hydrophobic polymer is a copolymer of polyvinylpyrrolidone and hexadecene, and the hydrophilic polymer is butylated polyvinylpyrrolidone.

11. The cosmetic composition of claim 10 wherein the talc coated with aluminum myristate comprises from about 10% to about 25% of the composition, the mica coated with aluminum myristate comprises from about 10% to about 30% of the composition, the low-luster pigment comprising mica, titanium dioxide, and barium sulfate comprises from about 5% to about 15% of the composition, the copolymer of polyvinylpyrrolidone and hexadecene comprises from about 1% to about 5% of the composition, and the butylated polyvinylpyrrolidone comprises from about 1% to about 5% of the composition.

12. The cosmetic composition of claim 10 further comprising skin-tone-dependent pigment selected from the group consisting of D & C Red No. 6, brown iron oxide and red iron oxide.

13. The cosmetic composition of claim 11 further comprising skin-tone-dependent pigment selected from the group consisting of D & C Red No. 6, brown iron oxide and red iron oxide, wherein the D & C Red No. 6 comprises up to about 15% of the composition, the brown iron oxide comprises up to about 15% of the composition, and the red iron oxide comprises up to about 15% of the composition.

14. The cosmetic composition of claim 1 wherein the emulsifier component is selected from the group consisting of sorbitan laurate, polysorbate 20, glyceryl monooleate, and tocopheryl acetate.

15. The cosmetic composition of claim 11 wherein the emulsifier component comprises all of sorbitan laurate, polysorbate 20, glyceryl monooleate, and tocopheryl acetate.

16. The cosmetic composition of claim 15 wherein the sorbitan laurate comprises from about 1% to 5% of the composition, the polysorbate 20 comprises from about 1% to about 5% of the composition, the glyceryl monooleate comprises from about 1% to about 5% of the composition, and the tocopheryl acetate comprises from about 0.5% to about 1% of the composition.

17. The cosmetic composition of claim 1 further comprising lauroyl lysine.

18. The cosmetic composition of claim 17 wherein the lauroyl lysine comprises from about 5% to about 15% of the composition.

19. The cosmetic composition of claim 1 further comprising a magnesium salt of a long-chain fatty acid selected from the group consisting of magnesium stearate, magnesium palmitate and magnesium arachidate.

20. The cosmetic composition of claim 19 wherein the magnesium salt of the long-chain fatty acid is magnesium stearate.

21. The cosmetic composition of claim 20 wherein the magnesium stearate comprises from about 2% to about 10% of the composition.

22. The cosmetic composition of claim 1 further comprising a preservative component.

23. The cosmetic composition of claim 22 wherein the preservative component is sodium dehydroacetate.

24. The cosmetic composition of claim 23 wherein the sodium dehydroacetate comprises from about 0.1% to about 1% of the composition.

25. The cosmetic composition of claim 1 further comprising trisodium ethylenediaminetetraacetate.

26. The cosmetic composition of claim 25 wherein the trisodium ethylenediaminetetraacetate comprises from about 0.05% to about 0.5% of the composition.

27. The cosmetic composition of claim 1 further comprising diisopropyl dimerate.

28. The cosmetic composition of claim 27 wherein the diisopropyl dimerate comprises from about 3% to about 8% of the composition.

29. A powder-based lip liner cosmetic composition comprising:
 (a) talc coated with aluminum myristate;
 (b) mica coated with aluminum myristate;
 (c) a low-luster pigment including mica, titanium dioxide, and barium sulfate;
 (d) a substantially hydrophobic polymer that is a polyvinylpyrrolidone/hexadecene copolymer;
 (e) hydrophilic polymer that is butylated polyvinylpyrrolidone;
 (f) an emulsifier component including sorbitan laurate, polysorbate 20, glyceryl monooleate, and tocopheryl acetate;
 (g) a skin-tone dependent pigment selected from the group consisting of D&C Red No. 6, brown iron oxide and red iron oxide;
 (h) lauroyl lysine;
 (i) magnesium stearate;
 (j) a preservative component that is sodium dehydroacetate;
 (k) trisodium ethylenediaminetetraacetate; and
 (l) diisopropyl dimerate; the mica component, the low-luster pigment, the substantially hydrophobic polymer, and the hydrophilic polymer each being present in a quantity sufficient to contribute to the appearance of the lips of a wearer to whom the composition is applied, and the emulsifier component being present in a quantity sufficient to emulsify the components including the substantially hydrophobic polymer and the hydrophilic polymer.

30. The cosmetic composition of claim 29 comprising the talc component from about 10% to about 25% of the composition, the mica component from about 10% to about 30% of the composition, the low-luster pigment comprises from about 5% to about 15% of the composition, the D & C Red No. 6 up to about 15% of the composition, the brown iron oxide up to about 15% of the composition, the red iron oxide up to about 15% of the composition, the butylated polyvinylpyrrolidone from about 1% to about 5% of the composition, the polyvinylpyrrolidone/hexadecene copolymer from about 1% to about 5% of the composition, the sorbitan laurate from about 1% to about 5% of the composition, the polysorbate 20 from about 1% to about 5% of the composition, the glyceryl monooleate from about 1% to about 5% of the composition, and the tocopheryl acetate from about 0.5% to about 1% of the composition.

31. A powder-based lip liner cosmetic composition comprising:

(a) about 10% to about 25% of talc coated with aluminum myristate;
(b) about 5% to about 15% of lauroyl lysine;
(c) about 10% to about 30% of mica coated with aluminum myristate;
(d) about 2% to about 10% of magnesium stearate;
(e) about 5% to about 15% of a low-luster pigment including mica, titanium dioxide, and barium sulfate;
(f) about 0.1% to about 1% of sodium dehydroacetate;
(g) about 0.05% to about 0.5% of trisodium ethylenediaminetetraacetate;
(h) about 1% to about 5% of an butylated polyvinylpyrrolidone;
(i) up to about 15% of D&C red No. 6;
(j) up to about 15% of brown iron oxide;
(k) up to about 15% of red iron oxide;
(l) about 1% to about 5% of sorbitan laurate;
(m) about 1% to about 5% of polysorbate 20;
(n) about 1% to about 5% of glyceryl monooleate;
(o) about 0.5% to about 1% of tocopheryl acetate;
(p) about 3% to about 8% of diisopropyl dimerate; and
(q) about 1% to about 5% of a copolymer of polyvinylpyrrolidone and hexadecene.

* * * * *